United States Patent
Shalaby et al.

(10) Patent No.: US 8,252,064 B2
(45) Date of Patent: *Aug. 28, 2012

(54) FIBER-REINFORCED COMPOSITE ABSORBABLE ENDOURETERAL STENT

(75) Inventors: Shalaby W. Shalaby, Anderson, SC (US); Kenneth W. Clinkscales, Easley, SC (US)

(73) Assignee: Poly-Med, Inc., Anderson, SC (US)

( * ) Notice: Subject to any disclaimer, the term of this patent is extended or adjusted under 35 U.S.C. 154(b) by 1485 days.

This patent is subject to a terminal disclaimer.

(21) Appl. No.: 11/346,117

(22) Filed: Feb. 2, 2006

(65) Prior Publication Data

US 2006/0178739 A1    Aug. 10, 2006

Related U.S. Application Data

(63) Continuation-in-part of application No. 11/204,822, filed on Aug. 16, 2005, now Pat. No. 8,083,805.

(60) Provisional application No. 60/650,240, filed on Feb. 4, 2005.

(51) Int. Cl.
*A61F 2/06*      (2006.01)
*A61F 2/04*      (2006.01)
*A61M 5/00*      (2006.01)

(52) U.S. Cl. .................. 623/23.66; 623/1.32; 623/1.33; 623/1.38; 623/1.5; 623/1.53; 623/1.54; 623/23.7; 604/8

(58) Field of Classification Search ........ 623/1.32–1.33, 623/23.64–23.66, 23.7–23.71; 604/8
See application file for complete search history.

(56) References Cited

U.S. PATENT DOCUMENTS

| | | | |
|---|---|---|---|
| 5,085,629 A | | 2/1992 | Goldberg et al. |
| 5,629,077 A | * | 5/1997 | Turnlund et al. ............. 623/1.15 |
| 6,045,568 A | * | 4/2000 | Igaki et al. .................. 623/1.11 |
| 6,174,330 B1 | * | 1/2001 | Stinson ........................ 623/1.34 |
| 6,342,065 B1 | * | 1/2002 | Shalaby ......................... 606/230 |
| 6,462,169 B1 | | 10/2002 | Shalaby |
| 6,524,345 B1 | | 2/2003 | Valimaa et al. |
| 6,585,773 B1 | | 7/2003 | Xie |
| 6,685,734 B1 | | 2/2004 | Valimaa et al. |
| 6,719,934 B2 | * | 4/2004 | Stinson ......................... 264/40.1 |
| 6,733,536 B1 | | 5/2004 | Gellman |
| 2001/0021873 A1 | * | 9/2001 | Stinson ........................ 623/1.34 |
| 2002/0031601 A1 | | 3/2002 | Darouiche et al. |
| 2002/0155159 A1 | | 10/2002 | Shalaby |
| 2002/0161168 A1 | | 10/2002 | Shalaby et al. |

(Continued)

FOREIGN PATENT DOCUMENTS

WO    WO0191668 A1    12/2001

OTHER PUBLICATIONS

Chew et al, "Advances in Uretral Stent Design and Construction," Contemporary Urology, Oct. 2004, p. 16.

(Continued)

*Primary Examiner* — Paul Prebilic
*Assistant Examiner* — Andrew Iwamaye
(74) *Attorney, Agent, or Firm* — McCormick, Paulding & Huber LLP

(57) ABSTRACT

Absorbable/disintegratable endourological stents, specifically endoureteral stents, and applicators for their introduction into the biological site, are formed from fiber-reinforced elastomeric films configured to prevent their migration from the application site.

26 Claims, 9 Drawing Sheets

U.S. PATENT DOCUMENTS

| | | |
|---|---|---|
| 2003/0069629 A1 | 4/2003 | Jadhav et al. |
| 2003/0120029 A1* | 6/2003 | Shalaby et al. ............... 528/310 |
| 2003/0162940 A1* | 8/2003 | Shalaby ........................ 528/425 |
| 2003/0209835 A1* | 11/2003 | Chun et al. .................... 264/339 |
| 2004/0138644 A1 | 7/2004 | DiCarlo et al. |
| 2004/0138738 A1 | 7/2004 | Stinson |
| 2004/0249441 A1* | 12/2004 | Miller et al. ................. 623/1.15 |

OTHER PUBLICATIONS

Finney, "Experience with New Double J Ureteral Catheter Stent," J. Urology, 120 (6), 578 (1978).

Beiko et al, "Urinary Tract Biomaterials," J. Urology, 171, 2438 (2004).

* cited by examiner

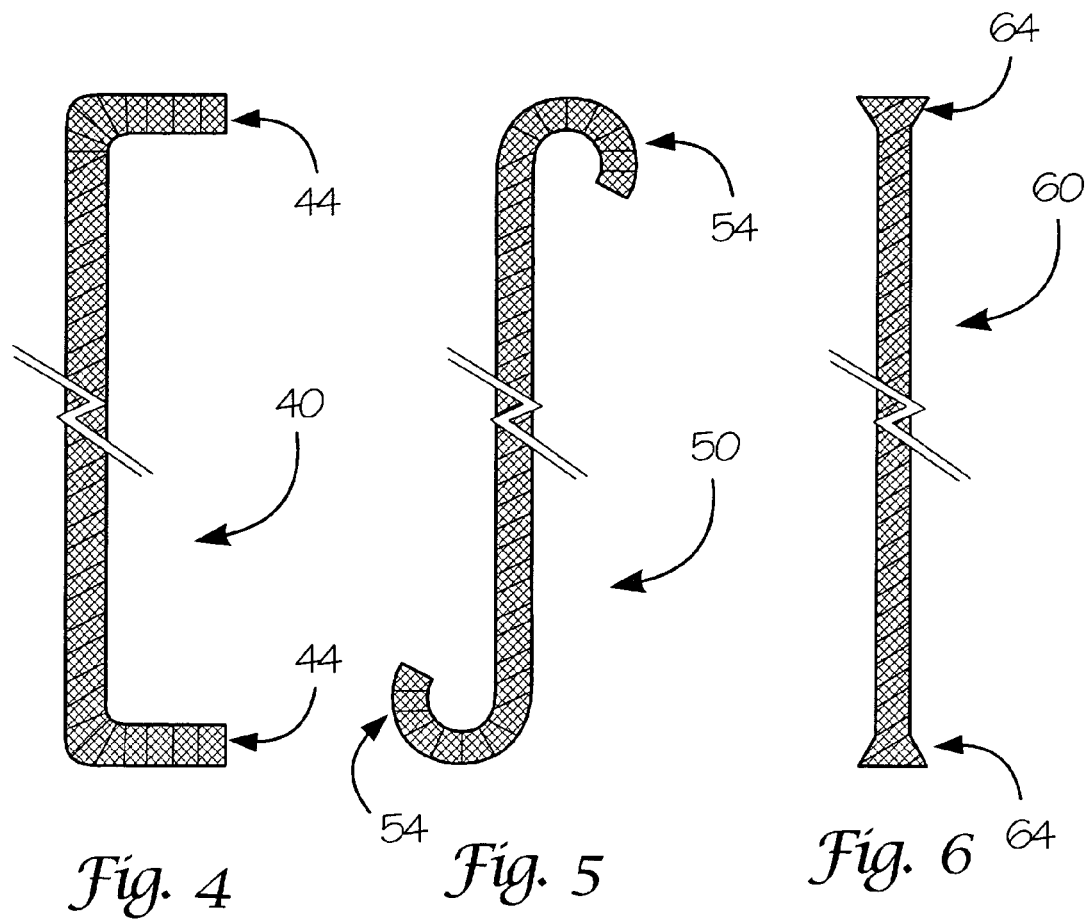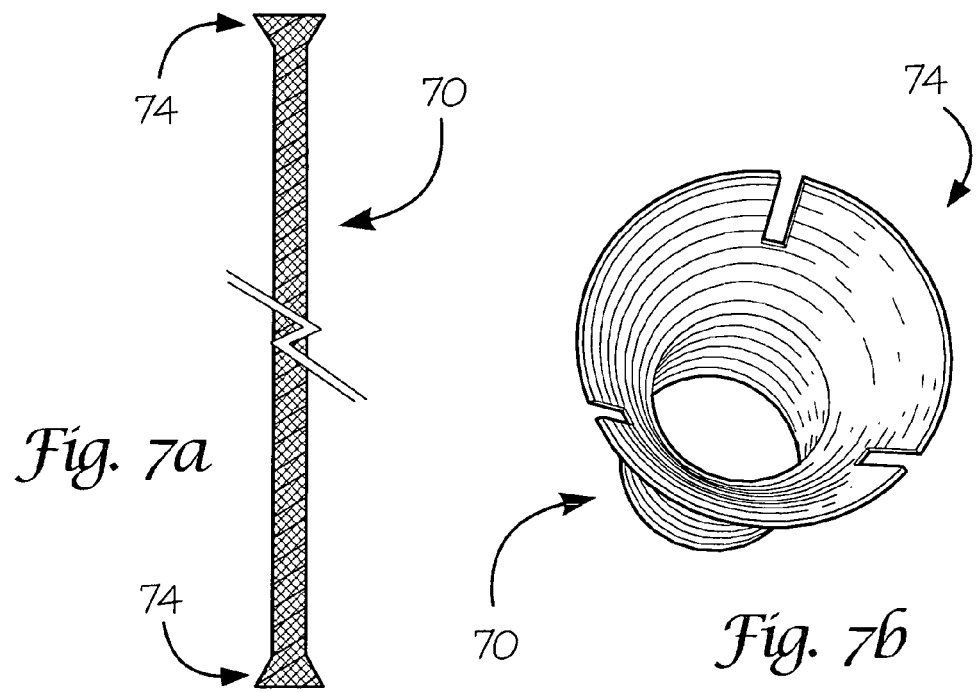

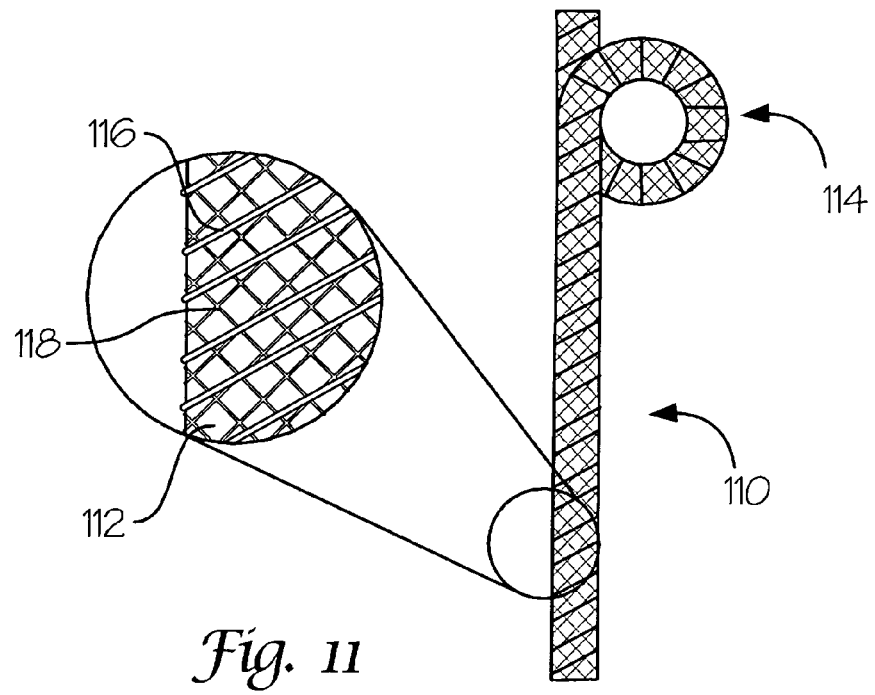
*Fig. 11*
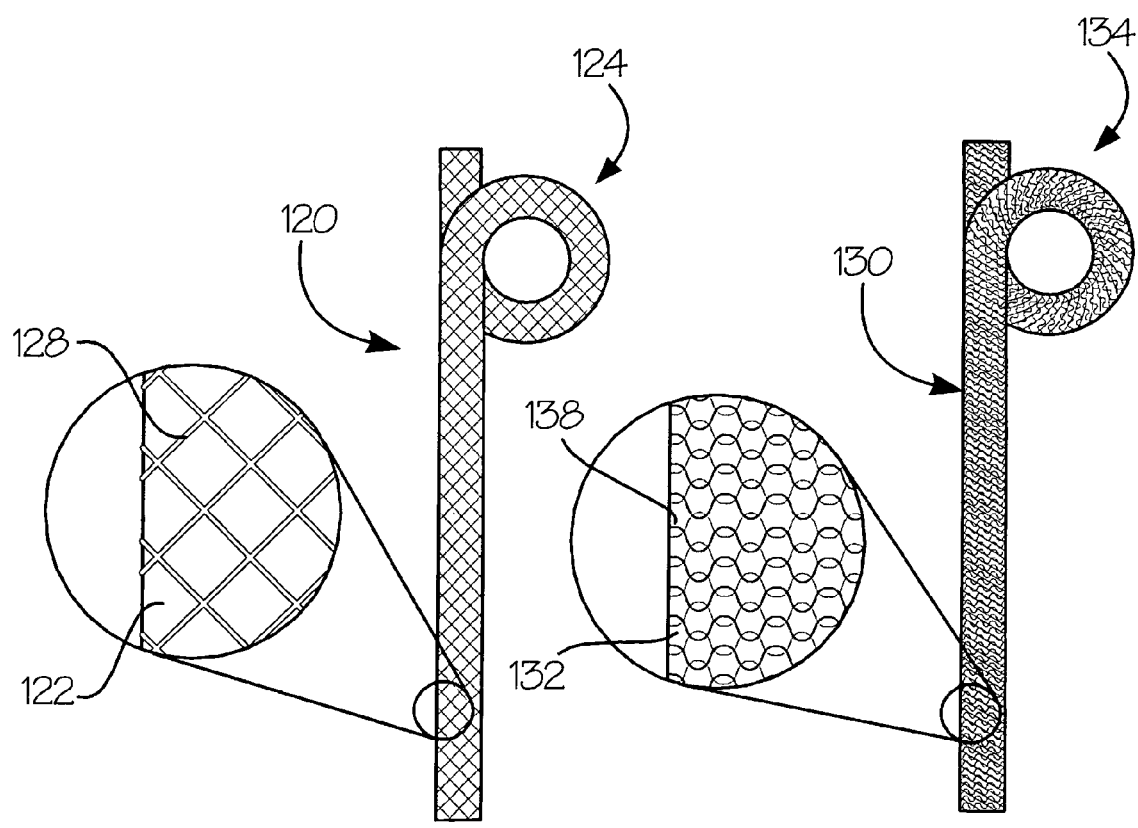
*Fig. 12*  *Fig. 13*

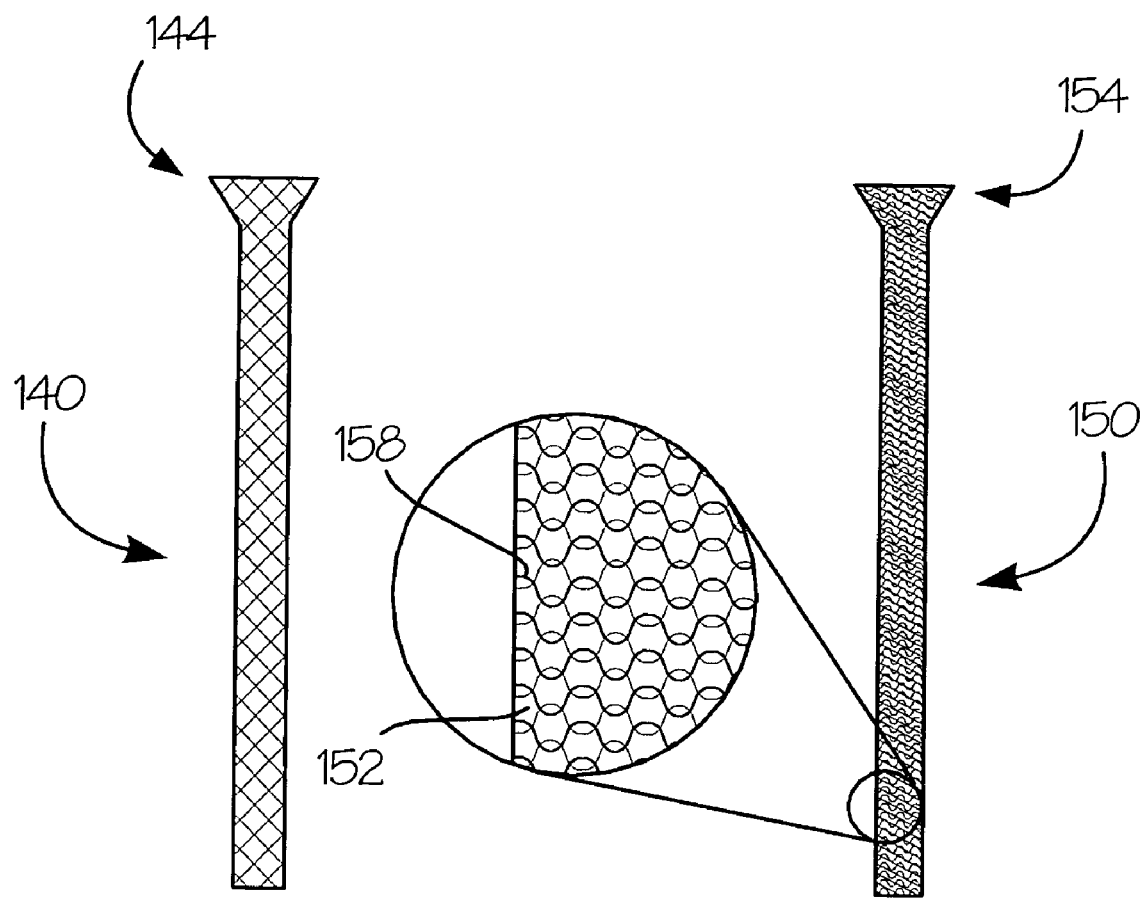

FIBER-REINFORCED COMPOSITE ABSORBABLE ENDOURETERAL STENT

This application claims the benefit of prior provisional application, U.S. Ser. No. 60/650,240, filed Feb. 4, 2005, and is a continuation-in-part application of U.S. Ser. No. 11/204,822, now U.S. Pat. No. 8,083,805, filed Aug. 16, 2005.

FIELD OF THE INVENTION

This invention relates to patient-customized, non-migrating, fiber-reinforced composite absorbable/disintegratable endoureteral stents and applicators therefor that are useful in maintaining optimum ureteral stent patency for a predetermined period of time. At the conclusion of this period, the stent is expected to have practically no physical presence that may interfere with pertinent biological functions.

BACKGROUND OF THE INVENTION

It has been reported that urinary stents and catheters have been used by ancient Egyptians in the form of papyrus and lead catheters (*Contemporary Urology*, October 2004, p. 16). Ureteral stents are a common tool in urologic practice. Since the development of the double-pigtail stent by Finney about three decades ago [*J. Urol.*, 120 (6), 578 (1978)], the search for the ideal stent continues; and patients continue to suffer from stent-related morbidity ranging from irritation and discomfort to sepsis and renal compromise from encrusted "forgotten" stents. During the search for the ideal endoureteral stent (E-stent) and related endo-urological devices, inventors and investigators of the prior art tried to exploit advances made in biomaterials, particularly absorbable or transient ones.

A typical illustration of the prior efforts is provided in U.S. Pat. No. 6,733,536 dealing with a urethral stent device. In this disclosure, a stent for treatment of a body lumen through which a flow is effected on either side of a sphincter was described, the stent comprising one or more windings and having an inner core substantially covered by an outer core and including a first segment, a second segment, and a connecting member disposed between the segments. When the stent is positioned within a patient's urinary system, the first segment and second segments are located on either side of the external sphincter to inhibit migration of the stent while not interfering with the normal functioning of the sphincter. The outer coating comprises an absorbable material that provides temporary structural support to the stent. After absorption of substantially all the outer coating of the stent, the remaining relatively compliant inner core facilitates easy removal by the patient by pulling a portion of the stent that extends outside the patient's body for this purpose.

In a review by Beiko and coworkers [*J. Urology*, 171, 2438 (2004)], it was noted that (1) the ideal substance for urinary tract biomaterial should incorporate certain features, such as biological inertness, chemical stability in urine, resistance to infection and encrustation, excellent long-term urinary flow, stability following placement, and no significant discomfort to the patient; and (2) urethral stents made of self-reinforced 80/20 l-lactide/glycolide copolymer were inserted in situ via cystoscopy into rabbit prostatic urethra and was found to be soft and almost completely degraded at three months—the material did not encroach into the urethral wall and there was no encrustation.

U.S. Pat. No. 6,585,773 describes an insertable stent for joining together and facilitating healing of adjacent tissues as in the case of sutureless end-to-end urethral and heterograft anastomosis. U.S. Pat. No. 6,685,734 describes a device for inserting a stent in a body cavity, particularly useful for inserting a stent into a human male urethra to treat prostatic hyperplasia, whereby such device has an elongated member for removably receiving a stent and means capable of protruding from the member to either locate an obstruction, such as the sphincter muscle, in the body cavity or to prevent the stent from sliding off of the member, or both. And U.S. Pat. No. 6,524,345 describes a suitable composition for constructing the stent described in U.S. Pat. No. 6,685,734. That composition comprises a biodegradable polymer interdispersed with ceramic particulates that are visible by radioscopy.

However, none of the prior art described a combination of absorbable endo-urological stent and non-absorbable applicator combination that permit facile insertion and secured location/maintenance of the stent at the intended site, wherein the insertion is associated with predictable change in stent configuration and dimensions to insure secure immobilization, prevent migration, maintain uninterrupted functionality over a predetermined period of time, and eventual safe, regulated disintegration and absorption. This provided an incentive for the present inventor to explore the use of contemporary absorbable biomaterials for the production of a novel endo-urological stent in copending U.S. patent application Ser. No. 60/600,336. The present invention extends to specific new designs of patient-customized, non-migrating, fiber-reinforced, absorbable/disintegratable endoureteral composite stents that are useful in maintaining optimum ureteral patency, for a predetermined period of time, while being securely placed in the ureteral tract.

SUMMARY OF THE INVENTION

This invention deals generally with absorbable/disintegratable, corrective devices and applicators therefor that are useful in maintaining optimum patency of conduits in the urinogenital tract as exemplified by endoureteral stents to maintain optimum ureteral patency for a predetermined period of time. At the conclusion of this period, the stent is expected to have practically no physical presence that may interfere with the normal biological function of the ureter.

An important aspect of this invention deals with an absorbable/disintegratable, multicomponent, non-migrating endoureteral stent which is a construct of a fiber-reinforced elastomeric film designed with at least one position-retaining end, wherein the fiber-reinforcement is (a) a combination of a monofilament coil and weft-knitted tube multifilament yarn; (b) a combination of monofilament coil and a braided multifilament yarn; (c) a tube comprising a braided or weft-knitted monofilament yarn; or (d) a weft-knitted or braided monofilament yarn in the form of a tube.

Another aspect of this invention deals with an absorbable/disintegratable, multi-component, non-migrating endoureteral stent which is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a slit tube, wherein the opposing edges of the slit tube form a protruding, flexible tab and can be compressively overlapped under stress within a rigid, tubular applicator to yield a partially rolled configuration having an outside diameter that is at least two percent less than that of the patient ureter and whenever the stress is released at the site of a renal conduit upon discharging from the tubular applicator the slit edges spring back to acquire a nominal diameter that is at least one percent larger than that of the biological conduit, leaving the end-tabs extended as position-retaining components.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the fiber-reinforced elastomeric film is in the form of a tube of a smaller diameter than that of the patient ureter, wherein each of the position-retaining ends defines two flexible flaps formed by incising the end of the tube to create a semicircular radial cut that is further slit vertically at the midline to form two freely, laterally deformable components.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the fiber reinforced elastomeric film is in the form of a tube with a central, main component having a smaller diameter than that of the patient ureter wherein each of the position-retaining ends defines two freely laterally deformable components formed of initially partially overlapping bitubular ends of the main, central component and a laterally fused tube which are radially and axially cut to produce two over-extended flaps attached to an intact semi-cylindrical extension of the main, central tube.

Another aspect of this invention deals with an absorbable/disintegratable, multi-component, non-migrating endoureteral stent which is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a tube with a smaller diameter than that of the patient ureter and having at least one position-retaining end, wherein the position-retaining end is an angled portion of the main tube having a length comparable to the patient ureter and comprising a flexible hinge that maintains an angle of more than 30° with respect to the main tube in an absence of deforming stress.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the fiber-reinforced film is tubular with a central main component having a smaller diameter than that of the patient ureter and comprising at least one position-retaining end wherein the position-retaining end is a highly flexible extension of the central main tube, acquiring a goose-neck shape after insertion in the patient ureter but can be made co-linear with the central main tube during insertion with an applicator.

An additional aspect of this invention deals with an absorbable/disintegratable, multi-component, non-migrating endoureteral stent which is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a tube having at least one position-retaining end, wherein the retaining end is an inverted cone having a diameter at the wider cross-section exceeding that of the main tube and that can be reversibly compressed to conform with the main tube diameter, which is also smaller than that of the patient ureter, upon applying radial compressive force in an applicator. It is preferred that the inverted cone is partially slit, yielding a cone wall having at least two leaflets and preferably three to five leaflets to facilitate the radial compression upon insertion with an applicator.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the elastomeric film is tubular with a central main component having a smaller diameter than that of the patient ureter and with at least one position-retaining end wherein the position-retaining end is an asymmetrically inverted cone with a teardrop cross-section, slit axially, at the peak of the teardrop which has an average diameter at the wider cross-section exceeding that of the central main tube wherein the slit asymmetric cone can be reversibly compressed to conform with the central main tube diameter upon applying radial compressive force in an applicator.

This invention also deals with an absorbable/disintegratable, multicomponent, non-migrating endoureteral stent which is a construct of a fiber-reinforced elastomeric film, wherein the fiber-reinforcement is a monofilament yarn or a combination with knitted or braided multifilament yarn, wherein the reinforced elastomeric film is tubular with a central main component that is a unilaterally, longitudinally crimped, inflatable tube having a circular cross-section that is smaller than that of the patient ureter when outwardly expanded, and having at least one position-retaining end wherein the position-retaining end is a unilaterally crimped, inflatable, asym-metric, inverted cone having a teardrop cross-sectional geometry and a crimp at the peak of the teardrop that is collinear with the crimp of the central main tube, wherein the average diameter of the inverted cone, when outwardly expanded, exceeds that of the central main tube.

A specific aspect of this invention deals with an absorbable/disintegratable, multi-component, non-migrating endoureteral stent which is a construct of a fiber-reinforced elastomeric film designed with at least one position-retaining end, wherein the film is formed of a segmented copolymer made from a polyethylene glycol and at least one cyclic monomer selected from the group represented by l-lactide, $\epsilon$-caprolactone, trimethylene carbonate, glycolide, a morpholine-dione, p-dioxanone, and 1,5-dioxapan-2-one, but preferably a mixture of $\epsilon$-caprolactone and glycolide. A typical composition of an elastomeric swellable film composition is a crystalline copolymer of a high molecular weight (20-35 kDa) polyethylene glycol (PEG) and 95/5 (molar) mixture of $\epsilon$-caprolactone/glycolide, wherein the weight percent of the PEG component in the copolymer is about 10 percent. Another typical composition of an elastomeric film composition is a crystalline segmented copolymer made in two steps. The first step entails the formation of an amorphous or low melting copolymer made from $\epsilon$-caprolactone, trimethylene carbonate and glycolide by polymerization in the presence of triethanolamine and stannous octanoate as the initiator and catalyst, respectively. In the second step, the product of the first step is reacted with a mixture of l-lactide and $\epsilon$-caprolactone to produce a crystalline triaxial final copolymer.

An additional aspect of this invention deals with an absorbable/disintegratable, multicomponent, non-migrating endoureteral stent which is a construct of a fiber-reinforced elastomeric film designed with at least one position-retaining end, wherein the fiber-reinforcement is a monofilament yarn or a combination with knitted or braided multifilament yarn, wherein the reinforcing monofilament yarn is formed of a segmented copolymer made from at least two cyclic monomers selected from the group represented by l-lactide, ε-caprolactone, trimethylene carbonate, glycolide, a morpholinedione, p-dioxanone, and 1,5-dioxapan-2-one, but preferably from l-lactide, ε-caprolactone, and trimethylene carbonate. The reinforcing monofilament yarn can also be a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. Furthermore, the reinforcing monofilament yarn can be a composite of an inorganic microparticulate dispersed phase of at least one material selected from the group consisting of barium sulfate, zirconium oxide, and absorbable phosphate glass and an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

Another specific aspect of the invention addresses an absorbable/disintegratable, multicomponent, non-migrating endoureteral stent which is a construct of a fiber-reinforced elastomeric film designed with at least one position-retaining end, wherein the fiber-reinforcement is a monofilament yarn or a combination with knitted multifilament or braided yarn, wherein the reinforcing knitted or braided multifilament fabric is formed of a crystalline segmented copolymer. A typical composition of such copolymer is a triaxial copolymer made in two steps. The first step entails the formation of an amorphous or low melting triaxial prepolymer using ε-caprolactone and/or trimethylene carbonate in the presence of trimethylolpropane and stannous octanoate as the initiator and catalyst, respectively. In the second step, the product of the first step is reacted with glycolide or a mixture of glycolide with ε-caprolactone and/or trimethylene carbonate. Another typical composition is a copolymer for use in producing knitted or braided multifilament yarn, which is a crystalline copolymer made from a polyethylene glycol and at least one cyclic monomer selected from the group represented by l-lactide, ε-caprolactone; trimethylene carbonate, glycolide, a morpholine-dione, p-dioxanone, and 1,5-dioxapan-2-one, but preferably from a polyethylene glycol, l-lactide, and trimethylene carbonate, and more preferably from a segmented copolymer of l-lactide and trimethylene carbonate.

A key aspect of this invention deals with an absorbable/disintegratable, multicomponent, non-migrating endoureteral stent which is a construct of a fiber-reinforced elastomeric film designed with at least one position-retaining end, wherein the fiber-reinforcement is a combination of a monofilament coil and a braided multifilament yarn, and wherein the film is formed of a crystalline segmented copolymer made from a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione. The film can also be formed from a crystalline segmented copolymer made from l-lactide and at least one cyclic monomer selected from the group consisting of glycolide, ε-caprolactone, trimethylene carbonate, p-dioxanone and 1,5-dioxepan-2-one, and a morpholinedione.

A key aspect of this invention deals with an absorbable/disintegratable, multicomponent, non-migrating endoureteral stent which is a construct of a fiber-reinforced elastomeric film designed with at least one position-retaining end, wherein the fiber-reinforcement is a combination of a monofilament coil and a braided multifilament yarn, and wherein the reinforcing monofilament yarn is formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing monofilament yarn is a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. The reinforcing monofilament yarn can also be a composite of an inorganic microparticulate dispersed phase of at least one material selected from the group of barium sulfate, zirconium oxide, and absorbable phosphate glass and an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

Another key aspect of this invention deals with an absorbable/disintegratable, multicomponent, non-migrating endoureteral stent which is a construct of a fiber-reinforced elastomeric film designed with at least one position-retaining end, wherein the fiber-reinforcement is a combination of a monofilament coil and a braided multifilament yarn, and wherein the reinforcing braided multifilament fabric is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one. Alternatively, the reinforcing braided multifilament tube is formed from a crystalline segmented copolymer of l-lactide and at least one cyclic monomer selected from the group consisting of glycolide, ε-caprolactone, trimethylene carbonate, p-dioxanone, 1,5-dioxepan-2-one, and a morpholinedione.

An important aspect of this invention deals with an absorbable/disintegratable, multicomponent, non-migrating endoureteral stent which is a construct of a fiber-reinforced elastomeric film designed with at least one position-retaining end, wherein the fiber-reinforcement is a tube of a braided or weft-knitted monofilament yarn, and wherein the fiber-reinforced film is tubular with a central main component having a smaller diameter than that of the patient ureter and having at least one position-retaining end, and wherein the position-retaining end is a highly flexible extension of the central main tube, acquiring a loop shape with an open end parallel to the axis of the central main tube after insertion in the patient ureter and the loop can be made co-linear with the central main tube during insertion with an applicator. The film component of the assembled stent is formed of a crystalline segmented copolymer made from a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione. Alternatively, the film is formed of a crystalline segmented copolymer made from l-lactide and at least one cyclic monomer selected from the group consisting of glycolide, ε-caprolactone, trimethylene carbonate, p-dioxanone and 1,5-dioxepan-2-one, and a morpholinedione.

Another important aspect of this invention deals with an absorbable/disintegratable, multicomponent, non-migrating endoureteral stent which is a construct of a fiber-reinforced elastomeric film designed with at least one position-retaining end, wherein the fiber-reinforcement is a tube of a braided or weft-knitted monofilament yarn, and wherein the reinforcing braided or weft-knitted monofilament yarn is formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing braided or weft-knitted monofilament yarn is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one. The reinforcing weft-knitted or braided monofilament can also be a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. Furthermore, the reinforcing weft-knitted or braided monofilament can be a composite of an inorganic microparticulate dispersed phase of at least one material selected from the group of barium sulfate, zirconium oxide, and absorbable phosphate glass and an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

A specific aspect of this invention deals with an absorbable/disintegratable, multicomponent, non-migrating endoureteral stent which is a construct of a fiber-reinforced elastomeric film designed with at least one position-retaining end, wherein the fiber reinforcement is a weft-knitted or braided monofilament scaffold and the reinforced construct therefrom is in the form of a tube comprising a central main component having a diameter smaller than that of the patient ureter and at least one position-retaining end, wherein the position-retaining end is an inverted cone having a series of diameters designed to provide progressively wider cross-sections than that of the central main tube and can be reversibly compressed to conform radially with the central main tube upon applying radial compressive force during insertion to the urinogenital tract using a tubular applicator, and wherein the film is formed of a crystalline segmented copolymer made from a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione. Alternatively, the film is formed of a crystalline segmented copolymer made from l-lactide and at least one cyclic monomer selected from the group consisting of glycolide, ε-caprolactone, trimethylene carbonate, p-dioxanone and 1,5-dioxepan-2-one, and a morpholinedione. Meanwhile, the reinforcing weft-knitted or braided monofilament yarn is formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing braided or weft-knitted monofilament yarn is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one.

Another specific aspect of this invention deals with an absorbable/disintegratable, multicomponent, non-migrating endoureteral stent which is a construct of a fiber-reinforced elastomeric film designed with at least one position-retaining end, wherein the fiber reinforcement is a weft-knitted or braided monofilament scaffold and the reinforced construct therefrom is in the form of a tube comprising a central main component having a diameter smaller than that of the patient ureter and at least one position-retaining end, wherein the position-retaining end is an inverted cone having a series of diameters designed to provide progressively wider cross-sections than that of the central main tube and can be reversibly compressed to conform radially with the central main tube upon applying radial compressive force during insertion to the urinogenital tract using a tubular applicator, and wherein the reinforcing weft-knitted or braided monofilament yarn is a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. Alternatively, the reinforcing braid or weft-knitted monofilament yarn is a composite of an inorganic microparticulate dispersed phase of at least one material selected from the group of barium sulfate, zirconium oxide, and absorbable phosphate glass, and wherein an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

A special aspect of this invention deals with an absorbable/disintegratable, multicomponent, non-migrating endoureteral stent which is a construct of a fiber-reinforced elastomeric film designed with at least one position-retaining end, wherein the fiber reinforcement is a weft-knitted monofilament yarn and the reinforced construct is in the form of a tube with a central main component having a smaller diameter than that of the patient ureter and having at least one position-retaining end wherein the position-retaining end is a highly flexible extension of the central main tube, acquiring a loop shape with an open end parallel to the axis of the central main tube after insertion in the patient ureter and the loop can be made co-linear with the central main tube during insertion with an applicator, and wherein the film is formed of a crystalline segmented elastomeric high l-lactide copolymer and the monofilament is formed of a segmented l-lactide copolymer with at least one cyclic monomer selected from the group consisting of glycolide, ε-caprolactone and a morpholinedione, and wherein the monofilament contains a microparticulate inorganic filler selected from the group of barium sulfate, zirconium oxide, and an absorbable phosphate glass.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the stent is capable of maintaining patency and remaining at the application site for at least two days, and preferably is capable of maintaining patency and remaining at the application site for two to four months.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the position-retaining ends contain at least four percent by weight of at least one powdered radiopacifier selected from the group represented by barium sulfate, zirconium oxide, and bismuth subcarbonate.

A clinically important aspect of this invention deals with an applicator for introducing the endoureteral stents which is a flexible polymeric catheter having lubricous inside and outside surfaces and a monofilament placement plunger with a solid end radially compatible with the internal diameter of the catheter.

Another clinically important aspect of this invention deals with an applicator for introducing the unilaterally crimped endoureteral stent illustrated in FIG. 10 into the urinogenital tract, which is a flexible catheter, a flexible guide-wire, and inflatable balloon with a pressurizing tube. Thus, inside the unilaterally crimped endoureteral stent are placed the balloon and the guide-wire and the assembly is then introduced into the ureter, through the patient urinogenital tract, with one position-retaining end at the entrance of the kidney to the ureter and an optional second end at the exit of the ureter to the bladder. When positioned at the biological site, the balloon is inflated to remove the longitudinal crimp and expand the endoureteral stent components to their original crimp-free dimensions. Then the balloon is deflated and the applicator assembly is removed from the patient.

BRIEF DESCRIPTION OF THE FIGURES OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

FIG. 4 is a side elevation view of another endoureteral stent in accordance with the present invention, in a planar configuration;

FIG. 5 is a side elevation view of another endoureteral stent in accordance with the present invention, in a planar configuration;

FIG. 6 is a side elevation view of another endoureteral stent in accordance with the present invention, in a planar configuration;

FIG. 7a is a side elevation view of another endoureteral stent in accordance with the present invention, in a planar configuration;

FIG. 7b is a perspective view of the stent of FIG. 7a in a curled configuration for use;

FIG. 11 is a side elevation view of another endoureteral stent in accordance with the present invention, in a planar configuration, with an exploded view of the fiber reinforcement;

FIG. 12 is a side elevation view of another endoureteral stent in accordance with the present invention, in a planar configuration, with an exploded view of the fiber reinforcement;

FIG. 13 is a side elevation view of another endoureteral stent in accordance with the present invention, in a planar configuration, with an exploded view of the fiber reinforcement;

FIG. 14 is a side elevation view of another endoureteral stent in accordance with the present invention, in a planar configuration; and FIG. 15 is a side elevation view of another endoureteral stent in accordance with the present invention, in a planar configuration, with an exploded view of the fiber reinforcement.

DETAILED DESCRIPTION OF PREFERRED EMBODIMENTS

Figure 1A:
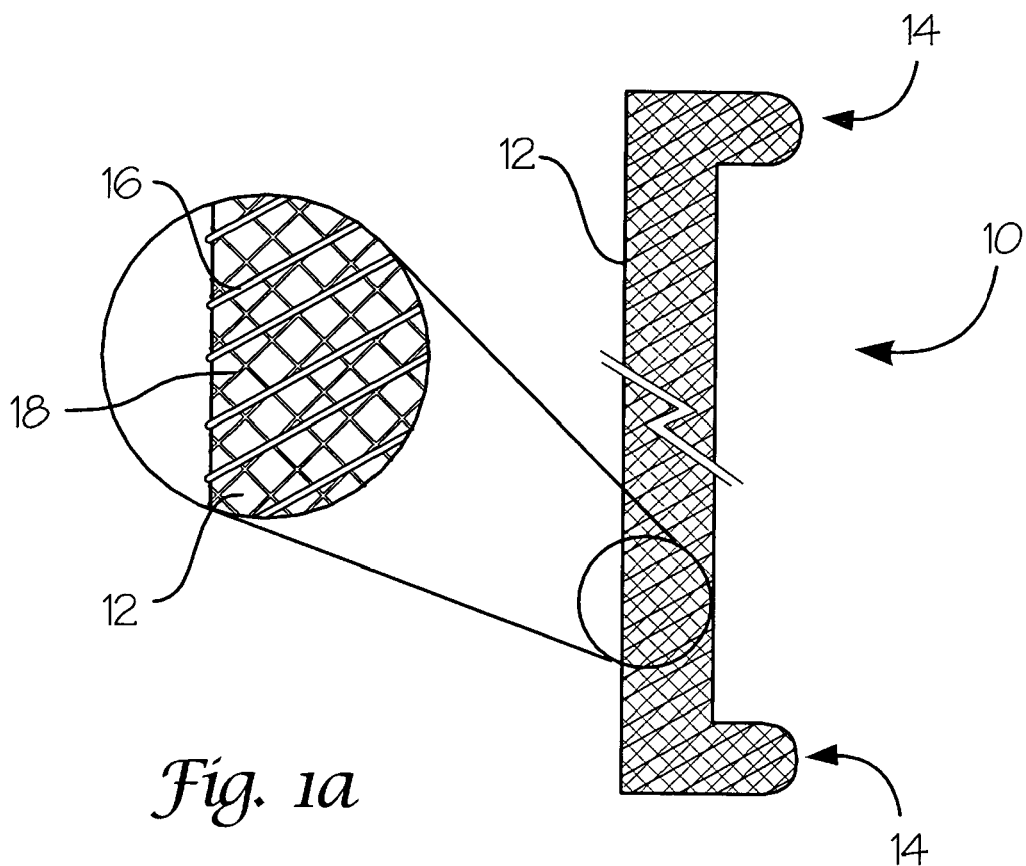
FIG. 1a is a side elevation view of an endoureteral stent in accordance with the present invention, in a planar configuration, with an exploded view of the fiber reinforcement.

An increasing geriatric population and associated complications due to compromised conduit functionality directed the attention of contemporary investigators to the use of absorbable, polymeric endourological stents to obviate the need for removal following the conclusion of their corrective function. Most, if not all, stents of the prior art have either tubular of spiral geometries that lack radial and/or axial elasticity/resilience leading to limited biomechanical compatibility and resistance to migration during end use and secured residence at the application site. This is particularly important in the case of endoureteral stents, which constantly experience pulsatile forces. The stent designs of the present invention address this issue. In effect, this invention deals with a variety of designs and modifications thereof, which can be configured to have at least one position-retaining end (or terminal) that prevents downward movement or extrusion from the patient ureter. When the device comprises two position-retaining ends, the device is stabilized against upward as well as downward movement. The simplicity of design allows their production in variable lengths that can be matched with ureters of almost all patients and, thus, can be denoted as patient-customized endoureteral stents. All designs call for the use of elastomeric film, water-swellable films reinforced with two types of fibrous components, both of which are slightly water-swellable. One component is a knitted tube comprising multifilament fibers adhering to a monofilament present in a helical configuration. All designs are radially resilient elastic constructs to permit synchronized changes in the device nominal diameter with those of the ureteral wall under prevailing pulsatile forces. From a design perspective, this invention also deals with a stent construct comprising (1) a highly oriented, monofilament-based scaffold or reinforcing filler that is radially strong and resilient to secure its mechanical stability at the application site; and (2) a crosslinked, highly compliant matrix to prevent premature extrusion of partially degraded fragments of the scaffold. A preferred feature of the present invention deals with having at least one component that swells readily in the biological environment to maximize the biomechanical compatibility of the device with the mucosal lining of the urinogenital conduits and more specifically those of ureters.

Although all the designs and corresponding compositions described in this invention pertain to endourological stents, some of the stents may be adopted for the production of absorbable endovascular stents, with and without the incorporating of a bioactive agent in the film to maintain vascular patency.

This invention deals generally with absorbable/disintegratable, corrective devices and applicators therefor that are useful in maintaining optimum patency of conduits in the urinogenital tract as exemplified by endoureteral stents to main optimum ureteral patency for a predetermined period of time. At the conclusion of this period, the stent is expected to have practically no physical presence that may interfere with the normal biological function of the ureter.

An important aspect of this invention deals with an absorbable/disintegratable, multicomponent, non-migrating endoureteral stent which is a construct of a fiber-reinforced elastomeric film designed with at least one position-retaining end, wherein the fiber-reinforcement is a monofilament or yarn or a combination with knitted or braided multifilament yarn.

Figure 1B:
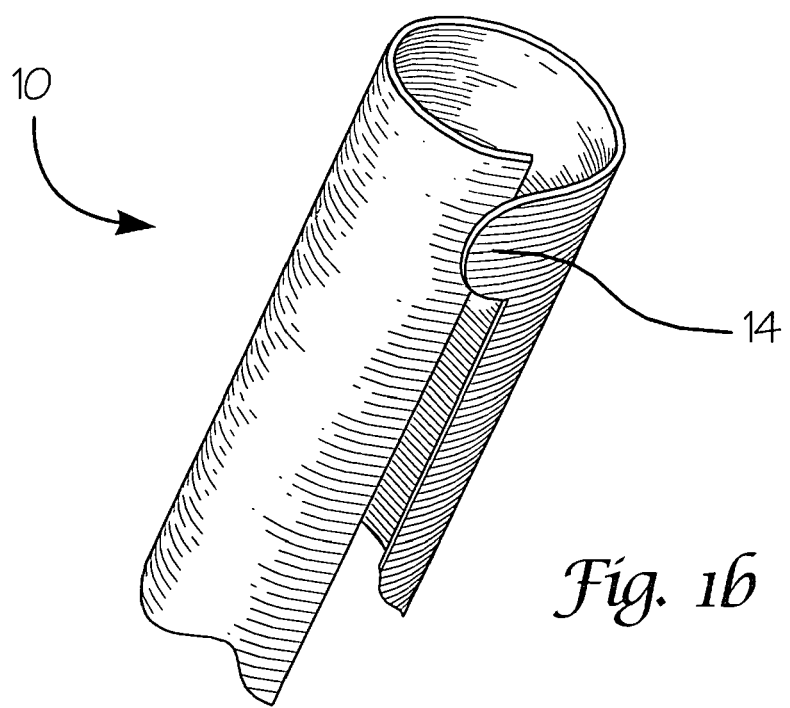
FIG. 1b is a perspective view of the stent of FIG. 1a in a curled configuration for use.

FIG. 1a illustrates an absorbable/disintegratable, multi-component, non-migrating endoureteral stent which is a construct 10 of a fiber-reinforced elastomeric film 12 having, in this embodiment, two position-retaining ends, tabs 14. The break in the construct length represents the variable, customizable length of the stent. For the present embodiment the fiber-reinforcement is a monofilament coil 16 in combination with a knitted multifilament yarn 18. As shown in FIG. 1b, the fiber-reinforced elastomeric film is in the form of a slit tube, wherein the opposing edges of the slit tube define protruding, flexible tabs that can be compressively overlapped under stress within a rigid, tubular applicator to yield a partially rolled configuration having an outside diameter that is at least two percent less than that of the patient ureter. When the stress is released at the site of a renal conduit upon discharging from the tubular applicator the slit edges spring back to acquire a nominal diameter that is at least one percent larger than that of the biological conduit, leaving the tabs 14 extended as position-retaining components.

Figure 2A:
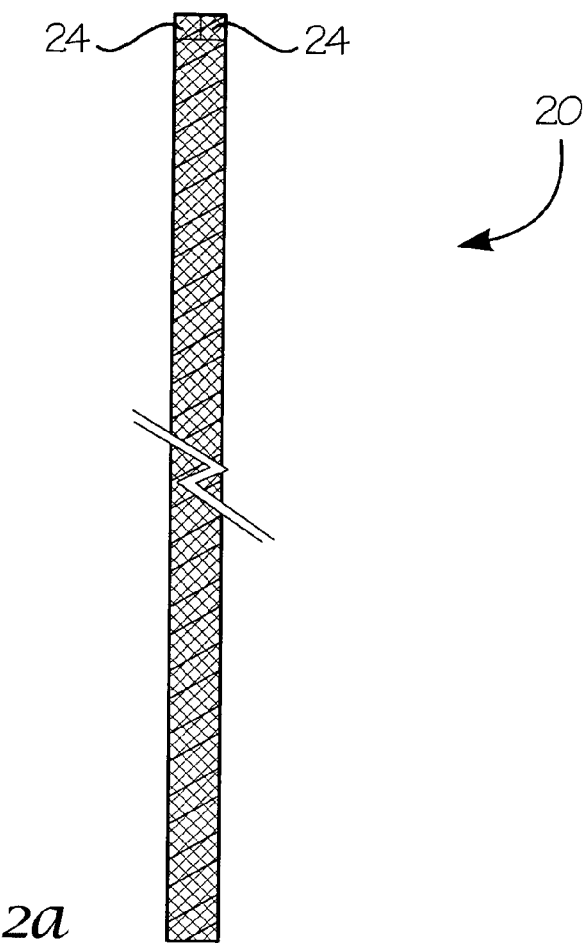
FIG. 2a is a side elevation view of another endoureteral stent in accordance with the present invention, in a planar configuration.
Figure 2B:
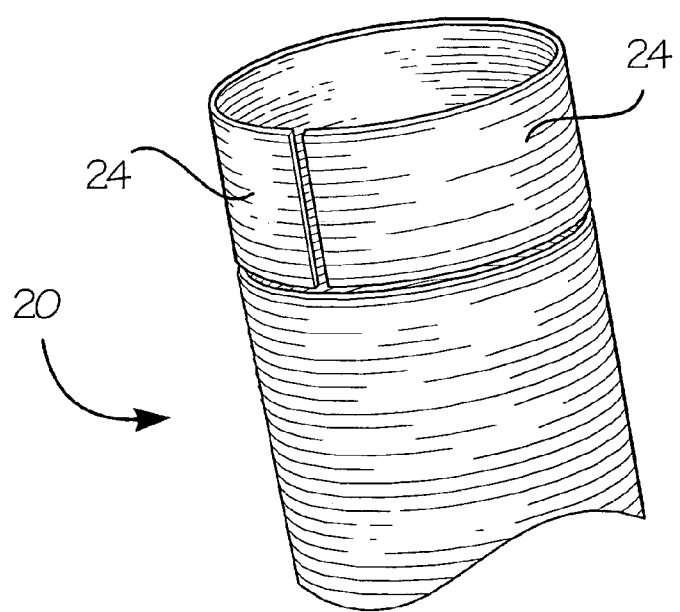
FIG. 2b is a perspective view of the stent of FIG. 2a in a curled configuration for use.

FIG. 2a illustrates an absorbable/disintegratable, multi-component, non-migrating endoureteral stent which is a construct 20 of a fiber-reinforced elastomeric film having at least one position-retaining end, which defines flaps 24. Here-again, the break in the construct length represents the customizable length of the stent. As in the embodiment of FIG. 1a, above, the present fiber reinforcement is a combination of a monofilament coil and a knitted multifilament yarn. As is shown in FIG. 2b, construct 20 is formed into a tube of a smaller diameter than that of the patient ureter, wherein each of the at least one position-retaining ends defines two flexible flaps 24 formed by incising the end of the tube to create a semicircular radial cut that is further slit vertically at the midline to form the two freely, laterally deformable components.

Figure 3A:
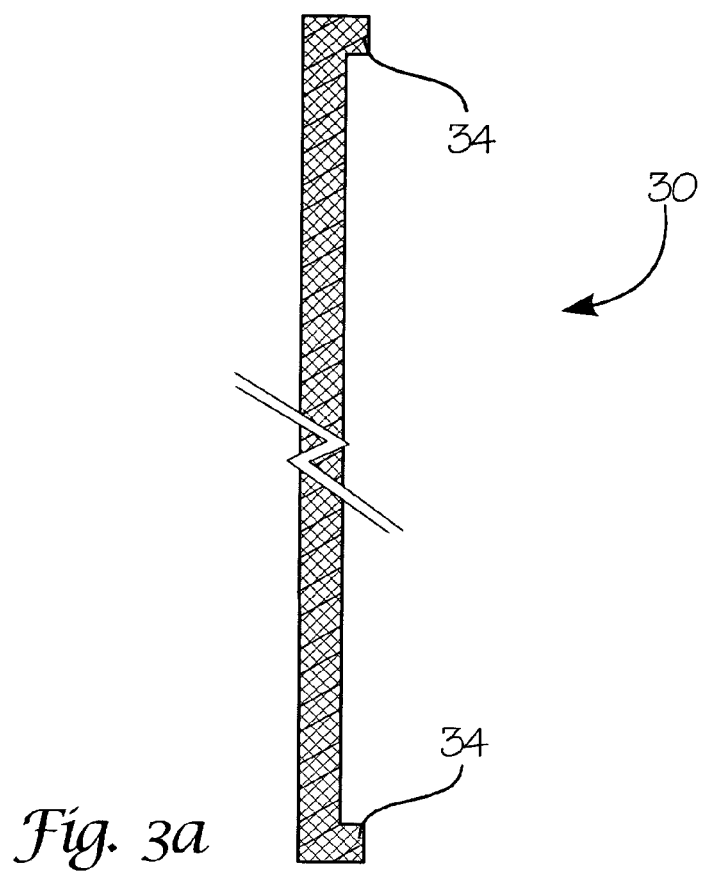
FIG. 3a is a side elevation view of another endoureteral stent in accordance with the present invention, in a planar configuration.
Figure 3B:
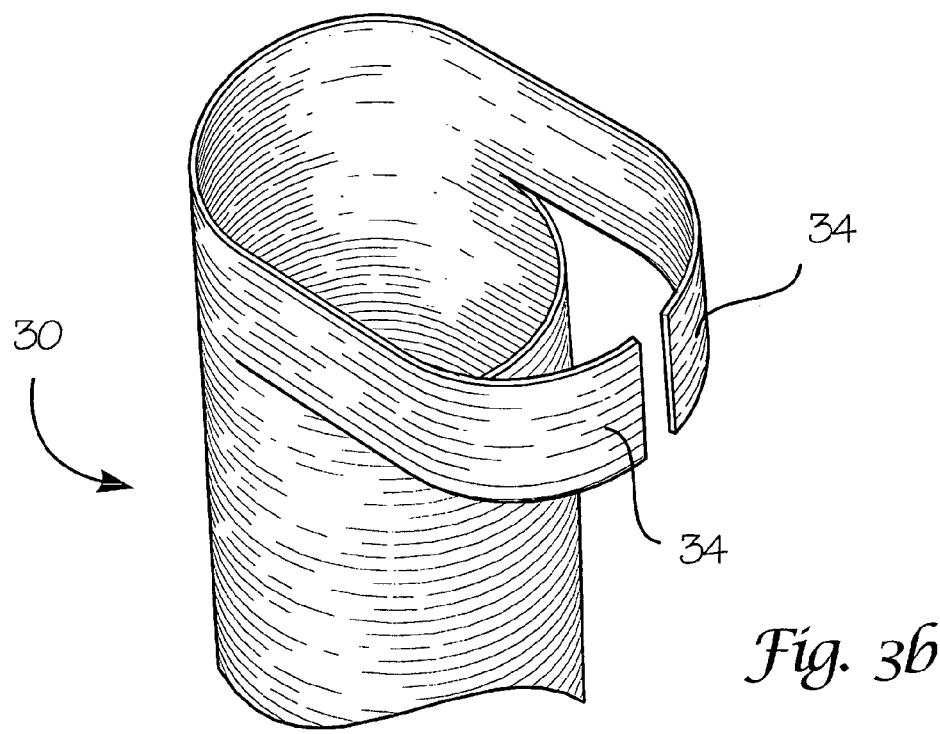
FIG. 3b is a perspective view of the stent of FIG. 3a in a curled configuration for use.

FIG. 3a illustrates an absorbable/disintegratable, multi-component, non-migrating endoureteral stent which is a construct 30 of the fiber-reinforced elastomeric film shown in the exploded view of FIG. 1a. This variable length construct, as shown, has two position-retaining ends. As can be seen from FIG. 3b, construct 30 is formed into a tube with a central, main component having a smaller diameter than that of the patient ureter. Each of the position-retaining ends defines two freely laterally deformable components 34 formed of initially partially overlapping bitubular ends of the main, central component and a laterally fused tube which are radially and axially cut to produce two over-extended flaps attached to an intact semi-cylindrical extension of the main, central tube.

FIG. 4 illustrates an absorbable/disintegratable, multi-component, non-migrating endoureteral stent which is a construct 40 of the fiber-reinforced elastomeric film shown in the exploded view of FIG. 1a. As shown, this variable length construct has two position-retaining ends. Construct 40 is in the form of a tube with a smaller diameter than that of the patient ureter and the position-retaining end is an angled portion 44 of the main tube having a length comparable to the patient ureter and comprising a flexible hinge that maintains an angle of more than 30° with respect to the main tube in an absence of deforming stress.

FIG. 5 illustrates an absorbable/disintegratable, multi-component, non-migrating endoureteral stent which is a construct 50 of the fiber-reinforced elastomeric film shown in the exploded view of FIG. 1a. As shown, this variable length construct has two position-retaining ends. Construct 50 is tubular with a central main component having a smaller diameter than that of the patient ureter and the position-retaining end is a highly flexible extension 54 of the central main tube, acquiring a goose-neck shape after insertion in the patient ureter but can be made co-linear with the central main tube during insertion with an applicator.

Figure 8A:
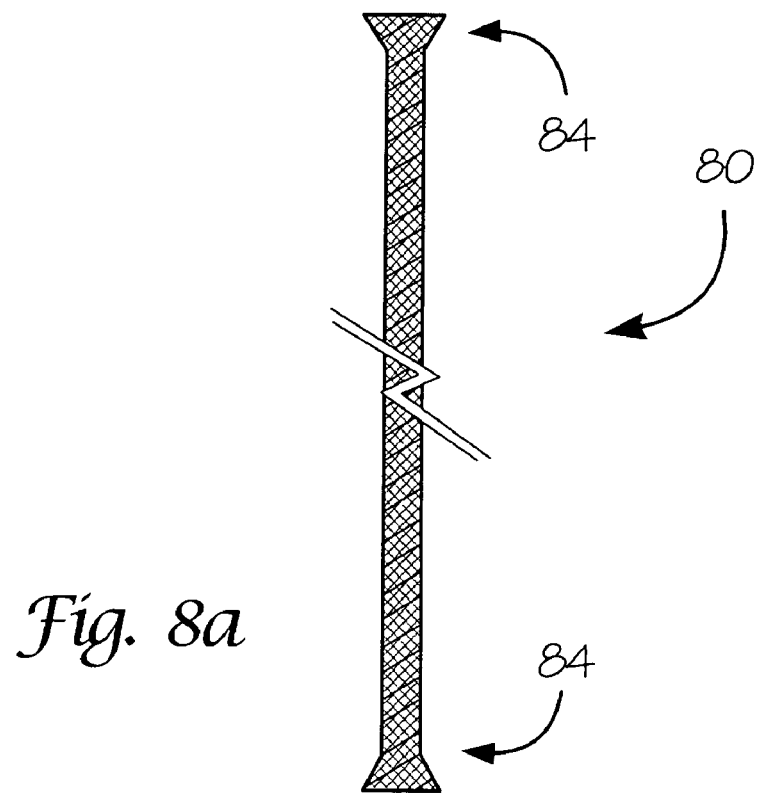
FIG. 8a is a side elevation view of another endoureteral stent in accordance with the present invention, in a planar configuration.
Figure 8B:
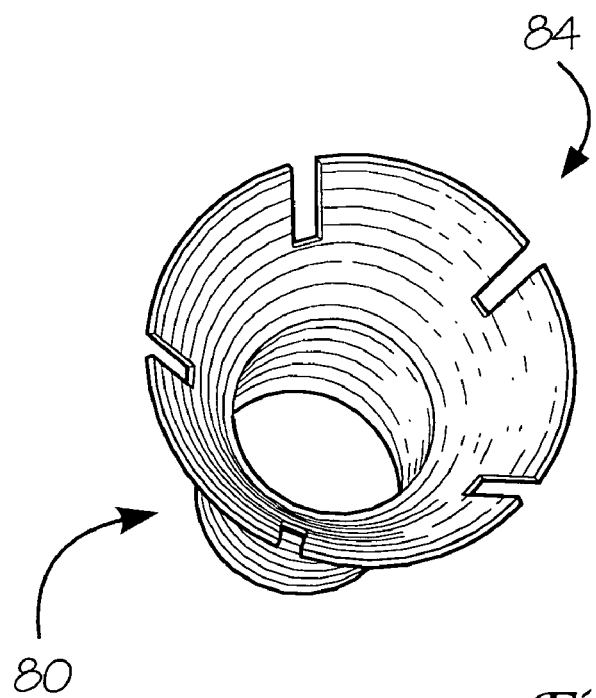
FIG. 8b is a perspective view of the stent of FIG. 8a in a curled configuration for use.

FIGS. 6, 7a, 7b, 8a and 8b illustrate absorbable/disintegratable, multi-component, non-migrating endoureteral stents which are constructs 60, 70, and 80, respectively, all formed of the same fiber reinforced elastomeric film as that discussed above with respect to FIG. 1a. For each of these embodiments the position retaining ends are in the form of an inverted cone (64, 74, and 84, respectively) having a diameter at the wider cross-section exceeding that of the main tube and that can be reversibly compressed to conform with the main tube diameter, which is also smaller than that of the patient ureter, upon applying radial compressive force in an applicator. As is best seen in FIGS. 7b and 8b, it is preferred that the inverted cone is partially slit, yielding a cone wall comprising at least two leaflets and preferably three (74) to five leaflets (84) to facilitate the radial compression upon insertion with an applicator.

Figure 9A:
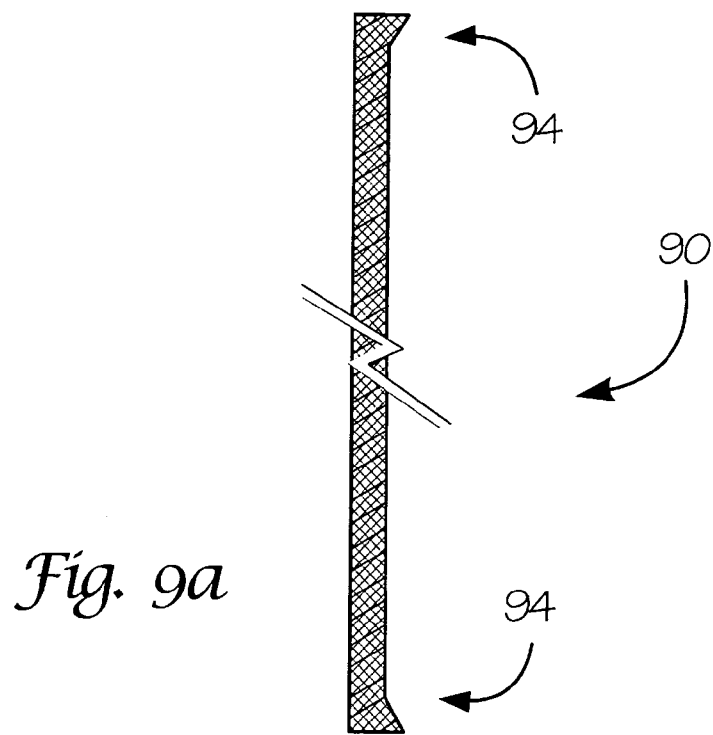
FIG. 9a is a side elevation view of another endoureteral stent in accordance with the present invention, in a planar configuration.
Figure 9B:
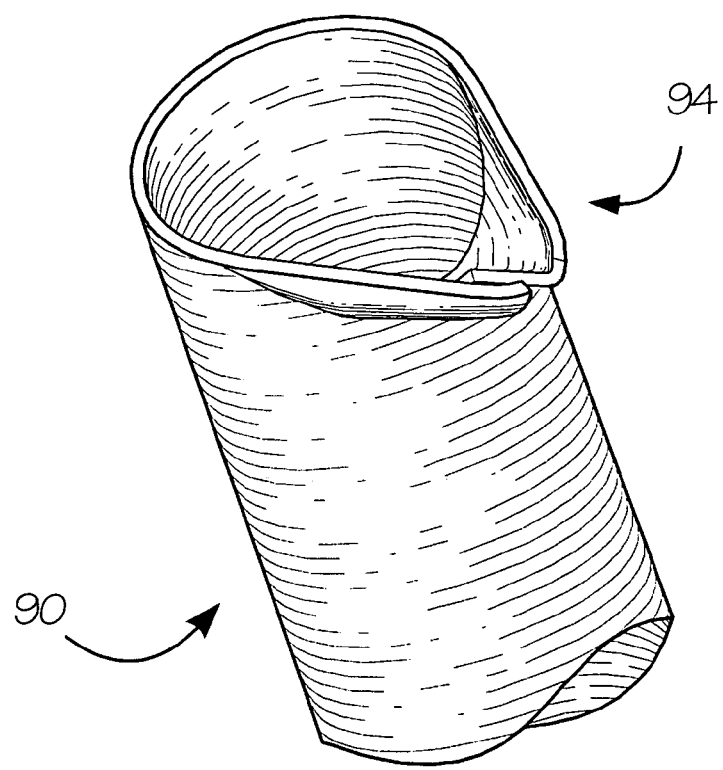
FIG. 9b is a perspective view of the stent of FIG. 9a in a curled configuration for use.

FIG. 9a illustrates an absorbable/disintegratable, multi-component, non-migrating endoureteral stent which is a construct 90 of the fiber-reinforced elastomeric film discussed above with respect to FIG. 1a. As shown, this variable length construct has two position retaining ends. As best seen in FIG. 9b, construct 90 is tubular with a central main component having a smaller diameter than that of the patient ureter, wherein the position-retaining end is an asymmetrically inverted cone 94 with a teardrop cross-section, slit axially, at the peak of the teardrop which has an average diameter at the wider cross-section exceeding that of the central main tube wherein the slit asymmetric cone can be reversibly compressed to conform with the central main tube diameter upon applying radial compressive force in an applicator.

Figure 10A:
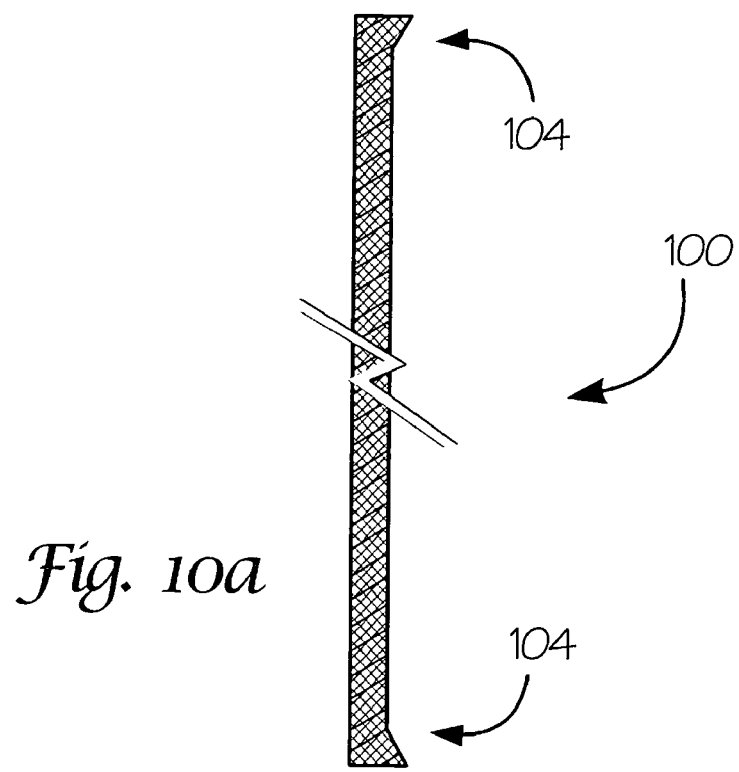
FIG. 10a is a side elevation view of another endoureteral stent in accordance with the present invention, in a planar configuration.
Figure 10B:
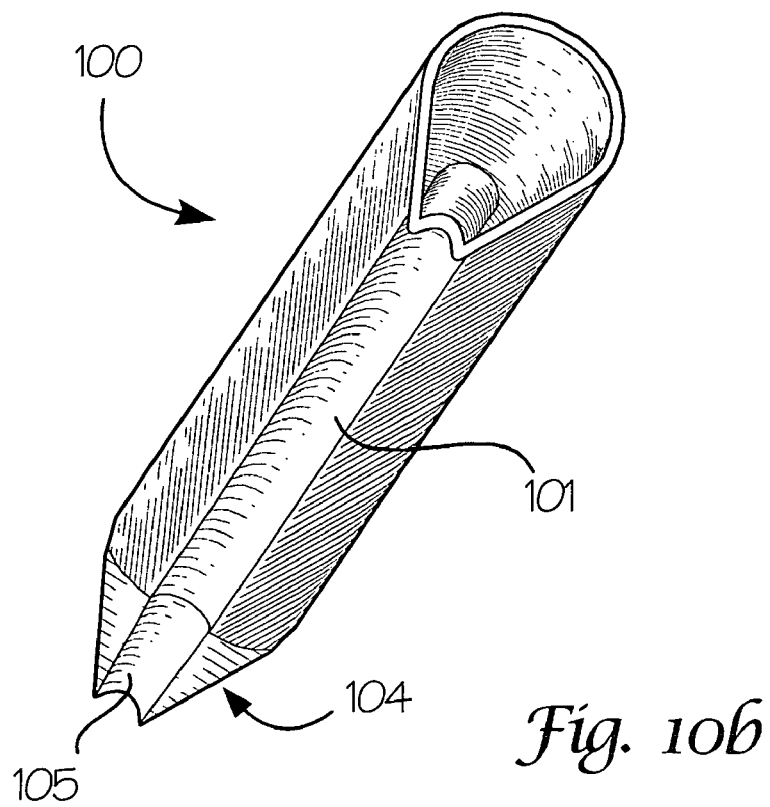
FIG. 10b is a perspective view of the stent of FIG. 10a in a curled configuration for use.

FIG. 10*a* illustrates an absorbable/disintegratable, multi-component, non-migrating endoureteral stent which is a construct 100 of the same fiber-reinforced elastomeric film shown in FIG. 1*a*. As is best seen in FIG. 10*b*, construct 100 is tubular with a central main component that is a unilaterally, longitudinally crimped (101), inflatable tube having a circular cross-section that is smaller than that of the patient ureter when outwardly expanded. Each of the position-retaining ends is a unilaterally crimped, inflatable, asym-metric, inverted cone 104 having a teardrop cross-sectional geometry and a crimp at the peak of the teardrop that is collinear with the crimp of the central main tube, wherein the average diameter of the inverted cone, when outwardly expanded, exceeds that of the central main tube.

FIG. 11 illustrates an absorbable/disintegratable, multi-component, non-migrating endoureteral stent which is a construct 110 of a fiber-reinforced elastomeric film 112 having, as is shown in this particular embodiment, one position-retaining end. Although not shown in this figure, the present stent may be of any desired length and include a second position-retaining end. For the present embodiment the fiber-reinforcement is a monofilament coil 116 in combination with a knitted multifilament tube 118. Construct 110 is tubular and the position-retaining end is a highly flexible extension of the central main tube, acquiring a loop shape 114 with an open end parallel to the axis of the central main tube after insertion in the patient ureter. The loop can be made co-linear with the central main tube during insertion with an applicator.

FIG. 12 illustrates an absorbable/disintegratable, multi-component, non-migrating endoureteral stent which is a construct 120 of a fiber-reinforced elastomeric film 122 having, as is shown in this particular embodiment, one position-retaining end. As discussed above with respect to the stent of FIG. 11, although not shown the present stent may be of any desired length and may include a second position-retaining end. For the present embodiment the fiber-reinforcement is a braided monofilament tube 128. Construct 120 is tubular and the position-retaining end is a highly flexible extension of the central main tube, acquiring a loop shape 124 with an open end parallel to the axis of the central main tube after insertion in the patient ureter. The loop can be made co-linear with the central main tube during insertion with an applicator.

FIG. 13 illustrates an absorbable/disintegratable, multi-component, non-migrating endoureteral stent which is a construct 130 of a fiber-reinforced elastomeric film 132 having, as is shown in this particular embodiment, one position-retaining end. As discussed above with respect to the stent of FIG. 11, although not shown the present stent may be of any desired length and may include a second position-retaining end. For the present embodiment the fiber-reinforcement is a weft-knitted monofilament 138. Construct 130 is tubular and the position-retaining end is a highly flexible extension of the central main tube, acquiring a loop shape 134 with an open end parallel to the axis of the central main tube after insertion in the patient ureter. The loop can be made co-linear with the central main tube during insertion with an applicator.

FIG. 14 illustrates an absorbable/disintegratable, multi-component, non-migrating endoureteral stent which is a construct 140 of a fiber-reinforced elastomeric film 142 having, as is shown in this particular embodiment, one position-retaining end. As discussed above with respect to the stent of FIG. 11, although not shown the present stent may be of any desired length and may include a second position-retaining end. For the present embodiment the fiber-reinforcement is a braided monofilament tube 148. Construct 140 is tubular and the position retaining end is in the form of an inverted cone having a diameter at the wider cross-section exceeding that of the main tube. Thus, the inverted cone can be reversibly compressed to conform to the main tube diameter, which is also smaller than that of the patient ureter, upon applying radial compressive force in an applicator. As was discussed above with respect to FIGS. 7*b* and 8*b*, although not shown the inverted cone may be partially slit, yielding a cone wall comprising at least two leaflets and preferably three to five leaflets to facilitate the radial compression upon insertion with an applicator.

FIG. 15 illustrates an absorbable/disintegratable, multi-component, non-migrating endoureteral stent which is a construct 150 of a fiber-reinforced elastomeric film 152 having, as is shown in this particular embodiment, one position-retaining end. As discussed above with respect to the stent of FIG. 11, although not shown the present stent may be of any desired length and may include a second position-retaining end. For the present embodiment the fiber-reinforcement is a weft-knitted monofilament 158. Construct 150 is tubular and the position retaining end is in the form of an inverted cone having a diameter at the wider cross-section exceeding that of the main tube. Thus, the inverted cone can be reversibly compressed to conform to the main tube diameter, which is also smaller than that of the patient ureter, upon applying radial compressive force in an applicator. As was discussed above with respect to FIGS. 7*b* and 8*b*, although not shown the inverted cone may be partially slit, yielding a cone wall comprising at least two leaflets and preferably three to five leaflets to facilitate the radial compression upon insertion with an applicator.

A specific aspect of this invention deals with an absorbable/disintegratable, multi-component, non-migrating endoureteral stent which is a construct of a fiber-reinforced elastomeric film designed with at least one position-retaining end, wherein the film is formed of a segmented copolymer made from a polyethylene glycol and at least one cyclic monomer selected from the group represented by l-lactide, ϵ-caprolactone, trimethylene carbonate, glycolide, a morpholine-dione, p-dioxanone, and 1,5-dioxapan-2-one, but preferably a mixture of F-caprolactone and glycolide.

An additional aspect of this invention deals with an absorbable/disintegratable, multi-component, non-migrating endoureteral stent which is a construct of a fiber-reinforced elastomeric film designed with at least one position-retaining end, wherein the fiber-reinforcement is a monofilament yarn or a combination with knitted or braided multifilament yarn, wherein the reinforcing monofilament yarn is formed of a segmented copolymer made from at least two cyclic monomers selected from the group represented by l-lactide, ϵ-caprolactone, trimethylene carbonate, glycolide, a morpholine-dione, p-dioxanone, and 1,5-dioxapan-2-one, but preferably from l-lactide, ϵ-caprolactone, and trimethylene carbonate.

Another specific aspect of the invention addresses an absorbable/disintegratable, multi-component, non-migrating endoureteral stent which is a construct of a fiber-reinforced elastomeric film designed with at least one position-retaining end, wherein the fiber-reinforcement is a monofilament yarn or a combination with knitted multifilament or braided yarn, wherein the reinforcing knitted or braided multifilament fabric is formed of a segmented copolymer made from a polyethylene glycol and at least one cyclic monomer selected from the group represented by l-lactide, ε-caprolactone, trimethylene carbonate, glycolide, a morpholine-dione, p-dioxanone, and 1,5-dioxapan-2-one, but preferably from a polyethylene glycol, l-lactide, and trimethylene carbonate, and more preferably from a segmented copolymer of l-lactide and trimethylene carbonate.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the stent is capable of maintaining patency and remaining at the application site for at least two days, and preferably is capable of maintaining patency and remaining at the application site for two to four months.

Another aspect of this invention deals with an absorbable/disintegratable, multi-component, non-migrating endoureteral stent which is a construct of a fiber-reinforced elastomeric film designed with at least one position-retaining end wherein the fiber reinforcement is a combination of a monofilament and knitted or braided multifilament yarn, wherein the position-retaining ends contain at least 4 percent by weight of at least one powdered radiopacifier selected from the group represented by barium sulfate, zirconium oxide, and bismuth subcarbonate.

A clinically important aspect of this invention deals with an applicator for inserting the endoureteral stents of FIGS. 1 through 9 and 11 through 15. Preferably such applicator is in the form of a flexible polymeric catheter having lubricous inside and outside surfaces and a monofilament placement plunger with a solid end radially compatible with the internal diameter of the catheter.

Another clinically important aspect of this invention deals with an applicator for introducing the unilaterally crimped endoureteral stent illustrated in FIG. 10, into the urinogenital tract. Preferably such applicator includes a flexible catheter, a flexible guide-wire, and an inflatable balloon with a pressurizing tube. Thus, inside the unilaterally crimped endoureteral stent are placed the balloon and the guide-wire and the assembly is then introduced into the ureter, through the patient urinogenital tract, with one position-retaining end at the entrance of the kidney to the ureter and an optional second end at the exit of the ureter to the bladder. When positioned at the biological site, the balloon is inflated to remove the longitudinal crimp and expand the endoureteral stent components to their original crimp-free dimensions. Then the balloon is deflated and the applicator assembly is removed from the patient.

Further illustrations of the present invention are provided by the following examples:

Example 1

Synthesis and Characterization of Polyethylene Glycol-ε-Caprolactone/Glycolide Block Copolymer for Use as a Swellable Elastomeric Film The reaction apparatus was comprised of a 100 mL boiling flask, magnetic stir bar, and one 90° connector for a nitrogen inlet. An initial charge consisting of ε-caprolactone (0.4163 moles, 47.5 g), glycolide (0.0219 moles, 2.5 g), and polyethylene glycol ($M_n$=35 kDa, 1.243×10$^{-4}$ moles, 4.38 g) was added to the kettle.

Using a temperature-controlled oil bath, the apparatus and its contents were heated to 50° C. and placed under vacuum for 45 minutes. The magnetic stir bar was stirring at a setting of 3.5. The system was then purged with nitrogen. To the final charge, a solution of 0.2 M of stannous octanoate in toluene (0.365 mL, 7.3×10$^{-5}$ moles,) was added. The temperature was increased to 160° C. The reaction was maintained at 160° C. for 2 hours.

The polymer was characterized for molecular weight in terms of inherent viscosity in chloroform (I.V.=2.51 dl/g). The melting temperature and heat of fusion were determined by differential scanning calorimetry ($T_m$=54.8° C. and $\Delta H_f$=63.4 J/g). The Mn and Mw were determined by GPC in dichloromethane ($M_n$=72.9 kDa and $M_w$=155 kDa).

Example 2

Synthesis and Characterization of Crystalline Segmented l-Lactide Copolymers for Use as Elastomeric Films: A General Method Crystalline segmented l-lactide copolymers comprising a triaxial copolymer comprising an amorphous core with crystalline grafts extending outward were prepared as per the general teaching of U.S. Pat. No. 6,462,169 (2002) and U.S. Pat. No. 6,794,485 (2004). For a typical copolymer (1) the core is made by the copolymerization of a mixture of trimethylene carbonate, ε-caprolactone, and glycolide in the presence of a stannous octanoate and triethanolamine as the catalyst and initiator, respectively; and (2) the crystalline end-grafts are formed by reacting the core copolymer with a mixture of l-lactide and ε-caprolactone. The resulting copolymer is characterized as described in Example 1.

Example 3

Preparation of Solutions for Film Casting

A General Method

A polymer from Example 1 or 2 was weighed and dissolved in acetone. Ratio of the solute to solvent was altered until desired consistency was achieved. A typical solution contained 4 percent polymer.

Example 4

Synthesis and Characterization of Crystalline Segmented l-Lactide Copolymers for Preparing Mesh Constructs: A General Method Copolymers were prepared in two steps from l-lactide and a small amount of trimethylene carbonate following the teaching of U.S. Pat. No. 6,342,065 (2002). Accordingly, a trimethylene carbonate (TMC) prepolymer is prepared using stannous octanoate, trimethylene glycol as the catalyst and initiator, respectively. The resulting prepolymer is then reacted with l-lactide containing a small fraction of TMC. The polymer is isolated and characterized in the usual manner as described in Example 1.

Example 5

Synthesis and Characterization of Crystalline Triaxial Segmented Glycolide Copolymers for Use in Coil Production: A General Method Crystalline triaxial segmented glycolide copolymers comprising a low melting or amorphous core with crystalline grafts extending outward were prepared as per general teaching of U.S. Pat. No. 6,462,169 (2002) and U.S. Pat. No. 6,794,485 (2004). For a typical copolymer (1) the core copolymeric component is made by the polymerization of ε-caprolactone and/or trimethylene carbonate in the presence of trimethylolpropane and stannous octanoate as the initiator and catalyst, respectively; and (2) the crystalline end-grafts are formed by reacting the core copolymer with a mixture of glycolide and ε-caprolactone. The copolymer was isolated and characterized as described in Example 1, with the exception of not using GPC for measuring the molecular weight due to insolubility in common GPC solvents.

Example 6

Synthesis of 35-65 Wt. Percent (40/20/40 mol %) ε-Caprolactone/l-Lactide/Glycolide-l-Lactide Copolymer for Use in Coil Production The reaction apparatus was comprised of a stainless steel reactor equipped with an overhead mechanical stirring unit, vacuum adapter, and nitrogen inlet. After attaining a vacuum≦0.5 mm Hg, the apparatus was purged with nitrogen. An initial charge consisting of 79.3 g (0.6954 moles) ε-caprolactone, 80.7 g (0.6954 moles) glycolide, 50.1 g (0.3477 moles) l-lactide, 0.376 g ($4.94 \times 10^{-3}$ moles) propanediol, and 0.7 mL ($1.39 \times 10^{-4}$ moles) of 0.2M solution of stannous octanoate catalyst in toluene was added to the reactor.

Using a high temperature oil bath, the apparatus and its contents were heated to 40° C. and placed under vacuum for 1.5 hours. The system was then purged with nitrogen. The temperature of the oil bath was increased to 160° C. Stirring began at 60 rpm. After approximately 2.25 hours at 160° C., the temperature was decreased to 80° C. (Note: the stirring rate was gradually decreased as the polymer became more viscous and was stopped when the temperature was approximately 115° C.) After approximately 15 hours at 80° C., the temperature was increased to 110° C. After 15 minutes at 110° C., a second charge of 0.7 mL ($1.39 \times 10^{-4}$ moles) of 0.2M solution of stannous octanoate catalyst in toluene was added to the apparatus while stirring slowly. The temperature was increased to 160° C. After approximately 1.75 hours at 160° C., the temperature was decreased to 130° C. A third charge of 390 g (2.7083 moles) l-lactide was added to the kettle while stirring at approximately 15 rpm. The stirring rate was gradually increased to 60 rpm. Once contents appeared to be completely and well mixed, the temperature was increased to 160° C. After approximately 0.5 hours, the stirrer was stopped. The reaction was maintained t 160° C. for 12 hours. The polymer was isolated, ground, purified, and characterized as described in Example 1.

The inherent viscosity using chloroform as a solvent was 1.65 dl/g. The molecular weight, $M_n$ and $M_w$, as determined by GPC using dichloromethane were 170.8 kDa and 248.5 kDa, respectively.

Example 7

Synthesis and Characterization of Composite High l-Lactide Segmented Copolymers for Use in Coil Production: A Typical Method The reaction apparatus was comprised of a stainless steel kettle equipped with an overhead mechanical stirring unit, vacuum adapter, and two nitrogen inlets. After attaining a vacuum≦10.5 mm Hg, the apparatus was purged with nitrogen. An initial charge of 200 grams barium sulfate was added to the kettle. (Note: $BaSO_4$ was sieved to remove any particles greater than 10μ in size before using.) The apparatus was then lowered into a high temperature oil bath that had been heated to 150° C.

The apparatus and its contents were placed under vacuum at 150° C. for 1.75 hour. The system was then purged with nitrogen. The temperature of the oil bath was decreased to 110° C. A second charge consisting of 89.6 grams (0.7860 moles) ε-caprolactone, 30.4 grams (0.262 moles) glycolide, 0.087 grams ($1.15 \times 10^{-3}$ moles) propanediol, and 0.0566 grams ($1.4 \times 10^{-4}$ moles) of stannous octanoate catalyst was added to the kettle. (Note: The second charge was dried in 40° C. vacuum oven for approximately 0.5 hours.) The temperature was increased to 180° C. After approximately 3 hours at 180° C., a second aliquot of 0.13 grams ($3.16 \times 10^{-4}$ moles) stannous octanoate catalyst was added to the kettle while stirring. After an additional 2 hours at 180° C., the temperature was decreased to 140° C. and the reaction was continued for an additional 16 hours. A final charge consisting of 180 grams (1.25 moles) l-lactide was added to kettle while stirring. Once contents appeared to be completely and well mixed, the temperature was increased to 170° C. After 5.5 hours, the temperature was decreased to 160° C. and the stirrer was stopped. The reaction was maintained at 160° C. for 17 hours.

The polymer was removed, ground, and dried. The ground polymer was dried under reduced pressure at room temperature and then at 40° C. After 2 hours at 40° C., the temperature of the oil bath was increased to 80° C. After 1 hour at 80° C., the temperature was increased to 110° C. Temperature was maintained at 110° C. for 4 hours.

The inherent viscosity using chloroform as a solvent was 1.05 dl/g. The molecular weight, $M_n$ and $M_w$, as determined by GPC using dichloromethane were 74 kDa and 132 kDa, respectively. The melting temperature and heat of fusion, as determined by differential scanning calorimetry, were 149.3° C. and 29.2 J/g, respectively.

Example 8

Synthesis and Characterization of Composite Segmented Copolymers of l-Lactide and Polyethylene Glycol for Use in Coil Production: A Typical Method Composite copolymers containing 40 percent $BaSO_4$ by weight were prepared and characterized as described in Example 7, with the exception of using polyethylene glycol having a molecular weight of 20 or 35 kDa as the initiator.

Example 9

Preparation of Monofilament and Multifilament Yarn for Coil and Mesh Production: A General Method Both the monofilament and multifilament yarns were prepared by melt-spinning the respective polymers, using a single- and multi-hole dies, respectively. The spinning processes for the high lactide copolymers for mesh or coil production were similar to those described in U.S. Pat. No. 6,342,065 (2002). On the other hand, the spinning processes for the high glycolide copolymers for coil production were similar to those descried in U.S. Pat. No. 6,255,408 (2001) and U.S. Pat. No. 6,462,169 (2002).

Example 10

Production of Weft-Knit Monofilament Scaffold for Endoureteral Stents

A Lamb circular weft knitting machine having a ⅞" cylinder and a 24-needle head with 24-gauge needles was used to make a knitted tube from a typical absorbable monofilament with diameter of about 150μ. A total of 12 needles were used to produce a knitted tube having a density of about 10 mg/cm².

A 1.9 mm Teflon rod was inserted into the knitted tube and the knitted tube was then attached to a tensioning rack. Once the tube is put under tension, the rack was placed into an oven at 110° C. for 15 minutes to heat-set the knitted construct. After the knit reached room temperature, the tension was released and the Teflon rod was removed to form a controlled size stent scaffold. The resulting annealed stent had an OD of 2.75-3 mm and a pore dimension of about 90×150μ. A tapered Teflon rod was used to heat-set and reshape one end of the knitted tube into an inverted cone. This can be used as a scaffold for an absorbable elastomeric film matrix to produce an endoureteral stent of the type shown in FIG. 15.

Example 11

Construction and Coating for Intact Tubular Designs

Scaffold Construction—Fibrous scaffolds of stent designs, illustrated in of FIGS. 2 and 6, were constructed by pulling a knitted sleeve of a multifilament yarn made from a segmented l-lactide/trimethylene carbonate copolymer, over a Teflon mold with the specific stents dimensions. After the sleeve was placed on the mold, the resulting assembly was heated in an air-circulating oven at 40° C. for 20 minutes to heat-set the knitted tube. Then an oriented monofilament yarn, made from a segmented l-lactide/trimethylene carbonate/ε-caprolactone copolymer, was used to wind tightly over the knitted tube on the mold in a single or double helix pattern. To prepare a reinforced elastomeric film, the fibrous construct assembly on the mold was dip-coated in the polymer solution of Example 2. The coated composite was allowed to dry on the Teflon mold in a laminar flow hood and then under reduced pressure at room temperature. For the designs with inverted cones, the composite tube was dipped for a second time, just at the ends, in a more concentrated solution to increase the rigidity and reliance of the coned ends after drying to a constant weight.

For the stent design of FIG. 1, a larger-diameter composite tube was prepared as described above and then cut into the final configuration.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. An absorbable, multicomponent, non-migrating endoureteral stent comprising:
   a tubular elastomeric film and a tubular fiber reinforcement, the tubular elastomeric film being a single tube covering the tubular fiber reinforcement,
   the stent defining at least one position-retaining end and a central main tube having a smaller diameter than that of a patient ureter, wherein the at least one position-retaining end is an extension of the central main tube, and the stent is configured to be positioned in the patient ureter and extend from a patient kidney to a patient bladder and to be retained in position by the at least one position-retaining end,
   the film reinforced with and impregnating the fiber-reinforcement, wherein the fiber-reinforcement comprises a monofilament coil disposed over a knitted or braided tube of a monofilament or multifilament yarn,
   the film and fiber reinforcement comprising an absorbable crystalline segmented copolymer comprising at least one cyclic monomer, and
   wherein the film and fiber reinforcement alone are capable of maintaining ureteral patency.

2. An absorbable, multicomponent, non-migrating endoureteral stent as in claim 1 wherein the at least one position-retaining end is a flexible extension of the central main tube, acquiring a goose-neck shape after insertion in the patient ureter but can be made colinear with the central main tube during insertion with an applicator.

3. An absorbable, multicomponent, non-migrating endoureteral stent as in claim 1 wherein the tubular elastomeric film comprises a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

4. An absorbable, multicomponent, non-migrating endoureteral stent as in claim 1 wherein the tubular elastomeric film comprises a crystalline segmented copolymer of l-lactide and at least one cyclic monomer selected from the group consisting of glycolide, ε-caprolactone, trimethylene carbonate, p-dioxanone and 1,5-dioxepan-2-one.

5. An absorbable, multicomponent, non-migrating endoureteral stent as in claim 1 wherein the monofilament coil comprises a crystalline segmented copolymer of at least two cyclic monomers selected from the group consisting of l-lactide, ε-caprolactone, trimethylene carbonate, glycolide, a morpholinedione, p-dioxanone and 1,5-dioxepan-2-one.

6. An absorbable, multicomponent, non-migrating endoureteral stent as in claim 1 wherein the monofilament coil comprises a composite comprising a polymeric matrix and an inorganic microparticulate dispersed phase contained within the matrix, the matrix comprising a crystalline segmented copolymer and the inorganic microparticulate dispersed phase comprising at least one material selected from the group consisting of barium sulfate, zirconium oxide, and absorbable phosphate glass.

7. An absorbable, multicomponent, non-migrating endoureteral stent as in claim 1 wherein the monofilament coil comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass.

8. An absorbable, multicomponent, non-migrating endoureteral stent as in claim 1 wherein the monofilament coil comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

9. An absorbable, multicomponent, non-migrating endoureteral stent as in claim 1 wherein the fiber-reinforcement comprises a monofilament coil and a braided tube of a multifilament yarn.

10. An absorbable, multicomponent, non-migrating endoureteral stent as in claim 9 wherein the tubular elastomeric film comprises a crystalline segmented copolymer of polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

11. An absorbable, multicomponent, non-migrating endoureteral stent as in claim 9 wherein the tubular elastomeric film comprises a crystalline segmented copolymer of l-lactone and at least one cyclic monomer selected from the group consisting of glycolide, ε-caprolactone, trimethylene carbonate, p-dioxanone, and 1,5-dioxepan-2-one, and a morpholinedione.

12. An absorbable, multicomponent, non-migrating endoureteral stent as in claim 9 wherein the monofilament coil comprises a crystalline segmented copolymer of at least two cyclic monomers selected from the group consisting of l-lactide, ε-caprolactone, trimethylene carbonate, glycolide, a morpholinedione, p-dioxanone, 1,5-dioxepan-2-one.

13. An absorbable, multicomponent, non-migrating endoureteral stent as in claim 9 wherein the monofilament coil comprises a composite comprising a polymeric matrix and an inorganic microparticulate dispersed phase contained within the matrix, the matrix comprising a crystalline segmented copolymer of at least two cyclic monomers selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass.

14. An absorbable, multicomponent, non-migrating endoureteral stent as in claim 9 wherein the monofilament coil comprises a composite comprising a polymeric matrix and an inorganic microparticulate dispersed phase contained within the matrix, the matrix comprising a crystalline segmented copolymer of a polyethylene glycol and at least two cyclic monomer selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass.

15. An absorbable, multicomponent, non-migrating endoureteral stent as in claim 9 wherein the multifilament yarn comprises a crystalline segmented copolymer of a polyethylene glycol and at least one cyclic monomer selected from the group consisting of l-lactide, trimethylene carbonate, ε-caprolactone, glycolide, p-dioxanone, a morpholinedione and 1,5-dioxepan-2-one.

16. An absorbable, multicomponent, non-migrating endoureteral stent as in claim 9 wherein the multifilament yarn comprises a crystalline segmented copolymer of l-lactide and at least one cyclic monomer selected from the group consisting of glycolide, ε-caprolactone, trimethylene carbonate, p-dioxanone, 1,5-dioxepan-2-one and a morpholinedione.

17. An absorbable, multicomponent, non-migrating endoureteral stent as in claim 1 wherein the monofilament coil is disposed over a tube of weft-knitted monofilament yarn.

18. An absorbable, multicomponent, non-migrating endoureteral stent as in claim 17 wherein the tubular elastomeric film comprises a crystalline segmented copolymer of polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

19. An absorbable, multicomponent, non-migrating endoureteral stent as in claim 17 wherein the tubular elastomeric film comprises a crystalline segmented copolymer of l-lactide and at least one cyclic monomer selected from the group consisting of glycolide, ε-caprolactone, trimethylene carbonate, p-dioxanone and 1,5-dioxepan-2-one, and a morpholinedione.

20. An absorbable, multicomponent, non-migrating endoureteral stent as in claim 17 wherein the monofilament yarn comprises a crystalline segmented copolymer of at least two cyclic monomers selected from the group consisting of l-lactide, ε-caprolactone, trimethylene carbonate, glycolide, a morpholinedione, p-dioxanone, and 1,5-dioxepan-2-one.

21. An absorbable, multicomponent, non-migrating endoureteral stent as in claim 17 wherein the monofilament yarn comprises a crystalline segmented copolymer of a polyethylene glycol and at least one cyclic monomer selected from the group consisting of l-lactide, trimethylene carbonate, ε-caprolactone, glycolide, p-dioxanone, a morpholinedione, and 1,5-dioxepan-2-one.

22. An absorbable, multicomponent, non-migrating endoureteral stent as in claim 17 wherein the monofilament yarn comprises a composite comprising a polymeric matrix and an inorganic microparticulate dispersed phase contained within the matrix, the matrix comprising a crystalline segmented copolymer of at least two cyclic monomers selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass.

23. An absorbable, multicomponent, non-migrating endoureteral stent as in claim 17 wherein the monofilament yarn comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass.

24. An absorbable, multicomponent, non-migrating endoureteral stent as in claim 1 wherein the stent is capable of maintaining patency and remaining at an application site for at least two days.

25. An absorbable, multicomponent, non-migrating endoureteral stent as in claim 1 wherein the stent is capable of maintaining patency and remaining at an application site for two to four months.

26. An absorbable, multicomponent, non-migrating endoureteral stent as in claim 1 wherein the at least one position-retaining end contains at least 4 percent by weight of at least one powdered radiopacifier selected from the group consisting of barium sulfate, zirconium oxide, and bismuth subcarbonate.

* * * * *